United States Patent
Wallace et al.

(10) Patent No.: US 6,312,725 B1
(45) Date of Patent: *Nov. 6, 2001

(54) RAPID GELLING BIOCOMPATIBLE POLYMER COMPOSITION

(75) Inventors: Donald G. Wallace, Menlo Park; Gregory M. Cruise, Fremont; Woonza M. Rhee, Palo Alto; Jacqueline Anne Schroeder, Boulder Creek; George T. Coker, III, Castro Valley; Marcee M. Maroney, Portola Valley, all of CA (US)

(73) Assignee: Cohesion Technologies, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/293,708

(22) Filed: Apr. 16, 1999

(51) Int. Cl.$^7$ .............................. A61K 9/14; A61K 31/74; B01J 13/00

(52) U.S. Cl. .................... 424/484; 424/485; 424/486; 424/488; 424/78.02; 424/78.06; 424/78.07; 424/DIG. 13; 427/2.14; 427/2.31; 427/331; 427/337; 427/340; 523/105; 523/111; 435/975

(58) Field of Search .................................. 424/484, 485, 424/486, 488, 78.02, 78.06, 78.07, DIG. 13; 427/2.14, 2.31, 209, 331, 337, 340; 523/105, 111; 435/975

(56) References Cited

U.S. PATENT DOCUMENTS

| | | |
|---|---|---|
| 5,292,362 | 3/1994 | Bass et al. ........................ 106/124 |
| 5,385,606 | 1/1995 | Kowanko . |
| 5,410,016 | 4/1995 | Hubbell et al. . |
| 5,496,872 | 3/1996 | Constancis et al. ................ 523/118 |
| 5,514,379 | 5/1996 | Weissleder et al. . |
| 5,583,114 | 12/1996 | Barrows et al. . |
| 5,618,551 | 4/1997 | Tardy et al. . |
| 5,629,294 | 5/1997 | DiZerega et al. . |

FOREIGN PATENT DOCUMENTS

| | | |
|---|---|---|
| 2809799 A1 | 9/1978 | (DE) . |
| 841 359 A1 | 5/1998 | (EP) . |
| 841 360 A1 | 5/1998 | (EP) . |
| 841 361 A1 | 5/1998 | (EP) . |
| WO 90/05755 | 5/1990 | (WO) . |
| WO 97/22371 | 6/1997 | (WO) . |
| WO 99/07417 | 2/1999 | (WO) . |
| WO 99/33419 | 7/1999 | (WO) . |

OTHER PUBLICATIONS

Bentley, M., "PEG Derivatives of Small Drug Molecules," *Shearwater Polymers, Inc.*, vol. 1, Issue 3 (Dec. 1998).
Bodanszky, M., *Principles of Peptide Synthesis*, 2$^{nd}$ Ed, Springer–Verlog, Berlin (1993) p. 21–37.
Braatz, James, et al., "A new hydrophilic polymer for biomaterial coatings with low protein adsorption," *J. Biomater. Sci. Polymer Edn.* (1992) 3(6):451–462.
Choi, Young, et al., "Star–Shaped Poly(ether—ester) Block Copolymers: Synthesis, Characterization, and Their Physical Properties," *Macromolecules* (1998) 31:8766–8774.
Ellis, D., et al., "The Ideal Tissue Adhesive in Facial Plastic and Reconstructive Surgery," *J. of Otolaryngol* (1990) 19:68–72.
Gelest, Inc., brochure, Tullytown, PA (1995).
Harris, J., Ed. *Poly(Ethylene Glycol) Chemistry: Biotechnical and Biomedical Applications* Plenum Press, New York, NY (1992), Chapter 22: "Synthesis of New Poly(Ethylene Glycol) Derivatives," Harris, J. et. al, p. 371–380.
Hendrick, J.L, et al., "Dendrimer–like Star Block and Amphiphilic Copolymers by Combination of Ring Opening and Atom Transfer Radical Polymerization," *Macromolecules* (1998) 31:8691–8705.
Hubbell, Jeffrey A., "Biomaterials in Tissue Engineering," *Bio/Technology* (1995) Jun.; 13:565–576.
Keys, Kelley, et al., "Poly(ethylene glycol) Star Polymer Hydrogels," *Macromolecules* (1998)31:8149–8156.
Leach, R., et al., "Reduction of Postoperative Adhesions in the rat Uterine Horn Model with Poloxamer 407," *Am. J. Obstet Gynecol.* (1990) 162:1317–1319.
Lin, Weiping, et al., "Thermosensitive Lactitol–Based Polyether Polyol (LPEP) Hydrogels," *Journal of Polymer Science: Part A: Polymer Chemistry* (1998) vol. 36:979–984.
Lundblad, R., *Chemical Reagents for Protein Modification*, 2$^{nd}$ Ed. CRC Press, Boca Raton, FL (1991), Chapter 6, "The modification of Cysteine," p. 59–93.
Rempp, P., et al., "Anionically Polymerized Star Macromolecules Having Divinylbenzene Cores with Grafted Poly (Ethylene Oxide) Arms as Biomaterials," *American Chemical Society, Polymer Division Symposium*, Boston. Apr., 1990. p. 12 only.

(List continued on next page.)

*Primary Examiner*—Nathan M. Nutter
(74) *Attorney, Agent, or Firm*—Dianne E. Reed; Laurie A. Axord

(57) ABSTRACT

This invention relates generally to two-part polymer compositions that rapidly form covalent linkages when mixed together. Such compositions are particularly well suited for use in a variety of tissue related applications when rapid adhesion to the tissue and gel formation is desired. In particular, they are useful as tissue sealants, in promoting hemostasis, for drug delivery, in effecting tissue adhesion, in providing tissue augmentation, and in the prevention of surgical adhesions.

40 Claims, 4 Drawing Sheets

OTHER PUBLICATIONS

Saito, H., et al., "Drug Delivery from Biodegradable PEG Hydrogels with Schiff Base Linkages," $23^{rd}$ Annual Meeting of the Society for Biomaterials, New Orleans, LA 1967.

Saunders, K.J., *Organic Polymer Chemistry*, pp. 353–356, 360–362, 374–375 Chapman and Hall, London (1973).

Shearwater Polymers, Inc., Catalog, *Polyethylene Glycol Derivatives* Huntsville, AL (1997–1998).

Shearwater Polymers, Inc., Course handout for "Biomedical and Biotechnical Applications of (Poly(Ethylene Glycol) Chemistry, A Short Course," Huntsville, AL, Jun. 25 & 26, 1998.

Texaco Chemical Company Brochure for *The JEFFAMINE Polyoxyalkyleneamines* (1985).

Wong, S., *Chemistry of Protein Conjugation and Cross–Linking*, pp. 81–85, 107–111, 113, 114–119, CRC Press, Boca Raton, FL (1991).

RAPID GELLING BIOCOMPATIBLE POLYMER COMPOSITION

FIELD OF THE INVENTION

This invention relates generally to two-part polymer compositions that rapidly form covalent linkages when mixed together. Such compositions are particularly well suited for use in a variety of tissue related applications when rapid adhesion to the tissue and gel formation is desired. In particular, they are useful as tissue sealants, in promoting hemostasis, for drug delivery, in effecting tissue adhesion, in providing tissue augmentation, and in the prevention of surgical adhesions.

BACKGROUND OF THE INVENTION

The use of polymer compositions in tissue engineering is now widely recognized, particularly those consisting of synthetic polymers. In contrast to many naturally derived compositions, synthetic polymer compositions can be formulated to exhibit predetermined physical characteristics such as gel strength, as well as biological characteristics such as degradability.

In a variety of tissue engineering applications, it is desirable to use compositions that can be administered as liquids, but subsequently form hydrogels at the site of administration. Such in situ hydrogel forming compositions are more convenient to use since they can be administered as liquids from a variety of different devices, and are more adaptable for administration to any site, since they are not preformed. Many different mechanisms have been described that can be used to promote hydrogel formation in situ. For example, photoactivatable mixtures of water-soluble co-polyester prepolymers and polyethylene glycol have been described to create hydrogel barriers, as well as drug release matrices. In another approach, block copolymers of Pluronic and Poloxamer have been designed that are soluble in cold water, but form insoluble hydrogels that adhere to tissues at body temperature (Leach, et al., *Am. J. Obstet. Gynecol.* 162:1317–1319 (1990)). Polymerizable cyanoacrylates have also been described for use as tissue adhesives (Ellis, et al., *J. Otolaryngol.* 19:68–72 (1990)). In yet another approach, two-part synthetic polymer compositions have been described that, when mixed together, form covalent bonds with one another, as well as with exposed tissue surfaces. (PCT WO 97/22371, which corresponds to U.S. application Ser. No. 08/769,806 U.S. Pat. No. 5,874,500.) In a similar approach involving a two-part composition, a mixture of protein and a bifunctional crosslinking agent has been described for use as a tissue adhesive (U.S. Pat. No. 5,583,114.)

One difficulty encountered when designing in situ hydrogel forming compositions is that optimizing the composition to enhance gel formation may worsen tissue inflammation at the site of administration. A possible explanation for this effect is that highly reactive composition components that are capable of rapid gel formation may adversely affect tissue surfaces.

The compositions of the present invention have been formulated to provide for rapid gelation, and also cause less tissue inflammation at the site of administration than previously described compositions.

SUMMARY OF THE INVENTION

The present invention discloses generally two-component polymer compositions that, when mixed together, rapidly react to form a matrix at the site of administration. Such compositions exhibit gel times of less than one minute. In one aspect of the present invention, one of the components is a sulfhydryl-containing compound. In another aspect of the present invention, both components contain multiple functional groups, and at least one of the compounds contains three or more functional groups. This ensures sufficient reactivity for formation of a three-dimensional polymer matrix. Preferably, both compounds contain four or more functional groups. For extremely fast reacting compositions, both compounds contain 12 functional groups.

In one aspect of the present invention, at least one and preferably both of the compounds are polymers. The non-reactive portion of the polymeric compound is referred to as its "core". Suitable polymer cores are synthetic polymers, polyamino acids, and polysaccharides. In a preferred embodiment, the core is a polyalkylene oxide, and more preferably it is polyethylene glycol.

The molecular weight of the compounds can vary depending on the desired application. In most instances, the molecular weight is about 100 to 1100,000 mol. wt., and more preferably about 1,000 to about 20,000 mol. wt. When the core material is polyethylene glycol, the molecular weight of the compound(s) is/are about 7,500 to about 20,000 mol. wt., and most preferaby they are about 10,000 mol. wt.

When only one of the compounds is a polymer, the other is a multifunctionally activated small organic molecule. Suitable small organic molecules include functionally activated succinimidyl and maleimidyl compounds.

The linkage group formed by reacting the two compounds of the present invention together is a covalent bond formed between the sulfur atom in the sulfhydryl group of one compound with, e.g., the carbon or sulfur atom in the sulfhydryl-reactive group of the other compound. The linkage may be a thioester, thioether or a disulfide, although a thioester linkage is preferred.

In another aspect of the present invention, the compounds further comprise chain extenders between the polymer core and the functional groups. Such chain extenders can activate or suppress reactivity of the functional groups, and can also be used to provide sites for hydrolysis or degradation. Suitable chain extenders include poly(amino acids), poly (lactones), poly(anhydrides), poly(orthoesters), poly (orthocarbonates), poly(phosphoesters), and enzymatically cleavable peptide groups.

The compositions of the present invention form gels with gel times of less than 1 minute, and more preferably less than 30 seconds, and most preferably less than 15 seconds. The strength (i.e., elastic modulus or G') of the resultant gels depends on the application for which the composition is adapted, but is preferably between about $10^2$ to $10^4$ dynes/$cm^2$ for a soft gel, or between about $10^5$ to $10^8$ for a harder gel.

In addition to the two reactive components of the compositions of the present invention, optional materials can also be included, such as glycosaminoglycans, proteins such as collagen, drugs, cells, hemostatic agents, genes, DNA, therapeutic agents, antibiotics, growth factors, and the like.

The compositions of the present invention are applied in liquid or solid form to the site of administration. It is also possible to supply them premixed but inactive, and then activate them at the site of administration.

In another aspect of the present invention, there is provided a method of treating tissues for the purpose of sealing tissues, preventing adhesions, providing a platform for delivery of biologically active agents, or augmenting tissues, comprising mixing together the two components as described herein at the site of administration to produce the desired medical affect.

DETAILED DESCRIPTION OF THE INVENTION

Figure 1:
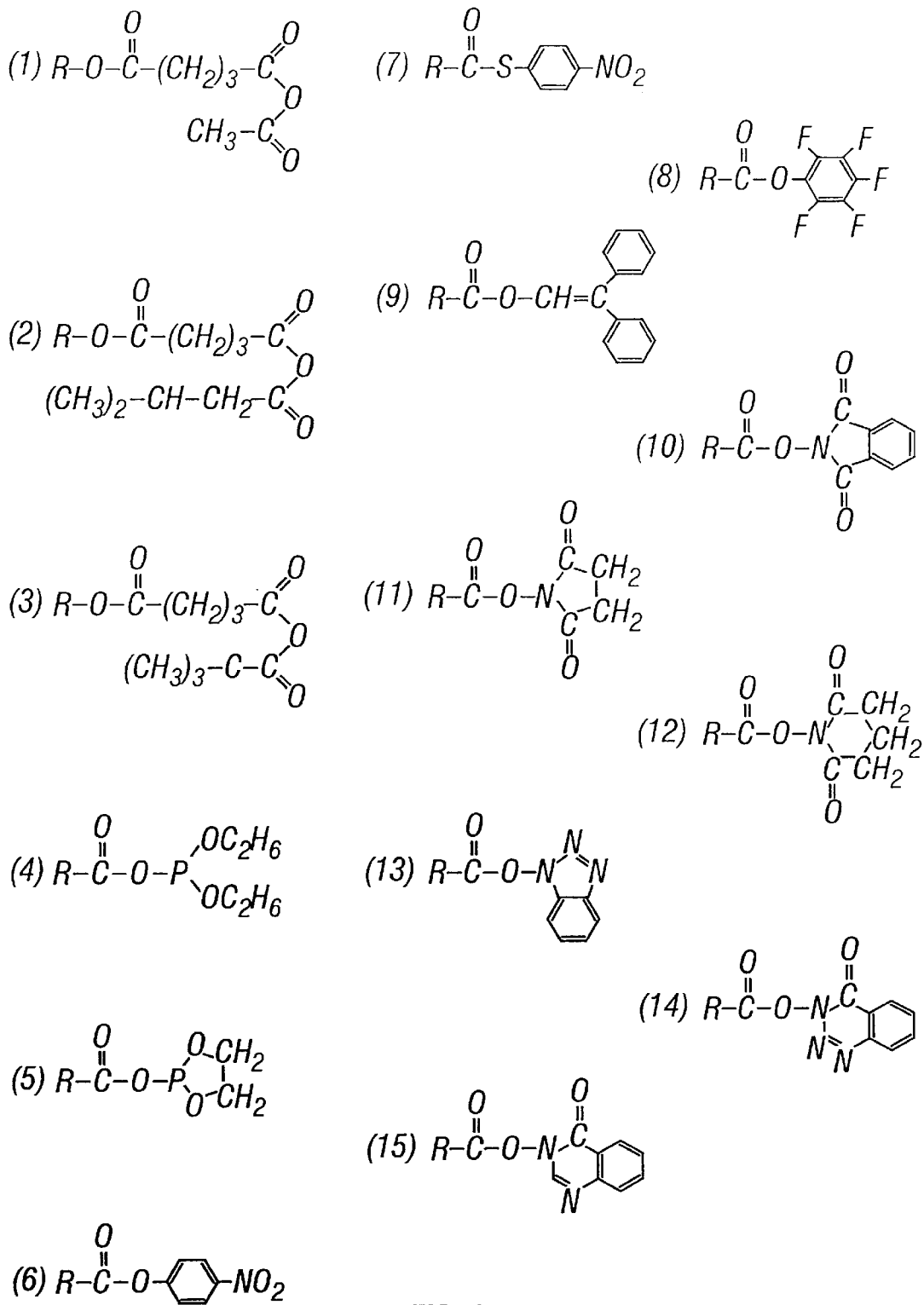
FIG. 1 depicts the structure of various sulfhydryl-reactive groups, with "R" representing the chemical structure to which the reactive group is attached.

The present invention relates to two-part polymer compositions that form a matrix when mixed together at the site of administration. Each component of the composition is generally administered separately to the tissue site. Then, within a very short time after being mixed together at the site of administration, the composition forms a gel with sufficient adhesive and cohesive strength to become anchored in place.

Definitions

The following definitions are provided to further describe various aspects of the preferred embodiments of the present invention.

The term "gel" refers to the state of matter between liquid and solid. As such, a "gel" has some of the properties of a liquid (i.e., the shape is resilient and deformable) and some of the properties of a solid (i.e., the shape is discrete enough to maintain three dimensions on a two dimensional surface.) Accordingly, "gelation time", also referred to herein as "gel time", refers to the time it takes for a composition to become non-flowable under modest stress. This is generally exhibited as achieving a gel strength, G', of greater than or equal to $10^2$ dynes/cm$^2$ in less than 1 minute.

The term "cohesive strength" refers to the ability of the compositions of the present invention to remain intact, i.e., not rupture, tear or crack, when subjected to physical stresses or environmental conditions. Cohesive strength is sometimes measured as a function of "burst strength".

The term "adhesive strength" refers to the ability of the compositions of the present invention to be able to remain attached to the tissues at the site of administration when subjected to physical stresses or environmental conditions.

The term "polymer" refers to a molecule consisting of individual chemical moieties, which may be the same or different, but are preferably the same, that are joined together. As used herein, the term "polymer" refers to individual chemical moieties that are joined end-to-end to form a linear molecule, as well as individual chemical moieties joined together in the form of a branched (e.g., a "multi-arm" or "star-shaped") structure.

The term "biocompatible" refers to the ability of the compositions of the present invention to be applied to tissues without eliciting significant inflammation and fibrosis or other adverse tissue responses.

The term "synthetic polymer" refers to polymers that are not naturally occurring and that are produced by chemical or recombinant synthesis. As such, naturally occurring proteins such as collagen and naturally occurring polysaccharides such as hyaluronic acid are specifically excluded. Proteins such as synthetic collagen, and carbohydrates such as synthetic hyaluronic acid, and their derivatives, are included.

The term "activated synthetic polymers" refers to synthetic polymers that have or have been chemically modified to have at least one functional group (e.g., a sulfhydryl group) that is capable of reacting with a corresponding reaction partner (e.g., a sulfhydryl-reactive group) to form a covalent bond. The term "multifunctionally activated" refers to synthetic polymers having two or more nucleophilic or electrophilic groups. Types of multifunctionally activated synthetic polymers include di-functionally activated, tri-functionally activated, tetra-functionally activated, and star-shaped activated polymers (that have four or more functional groups).

Composition Components

The two-part compositions of the present invention comprise two different compounds, each within a separate part of the composition and at least one of which is a polymer, that react with one another to form a covalently crosslinked gel matrix. As such, they can easily be administered separately, and rapidly form gels at the site of administration.

In the compositions of the present invention, each component is present in one of the two separate parts, or "components", of the composition, along with other optional ingredients as described elsewhere herein. The two reactive compounds and the gel matrix that forms when they are mixed together can be represented by Formula I as follows:

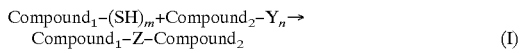

Compound$_1$–(SH)$_m$+Compound$_2$–Y$_n$→
   Compound$_1$–Z–Compound$_2$    (I)

Compound$_1$ has multiple (m≧2) sulfhydryl groups (SH) that react with Compound$_2$, which has multiple (n≧2) sulfhydryl-reactive groups (Y). It should be understood that sulfhydryl groups are also "sulfhydryl reactive groups", since it is well known that sulfhydryl groups will react with one another under certain conditions. When mixed together, the two compounds become interconnected via a covalent bond (Z). As depicted in FIG. 1 for illustration purposes only, there is only one bond formed between Compound$_1$ and Compound$_2$. However, when m+n≧5, and appropriate ratios of the two components are utilized as described elsewhere herein, the two compounds form multiple attachments to one another resulting in a three-dimensional polymer matrix. Preferably, both compounds contain four or more functional groups, since such multifunctionality results in a gel matrix with greater overall cohesive strength. In a particularly preferred embodiment, each of the compounds is tetrafunctionally activated.

In another preferred embodiment, the compounds each have 12 functional groups. Such compounds are formed from reacting a first tetrafunctionally activated polymer with a second tetrafunctionally activated polymer, wherein the functional groups of each of the two compounds are a reaction pair, and react together to form "12-arm" functionally activated polymers. An example of such a "12-arm" compound is dodeca-sulfhydryl-PEG, 50,000 mol. wt., which is constructed from a core tetra-functional succinimide ester PEG coupled to four (exterior) tetra-functional sulfhydryl-PEG molecules. Such polymers range in size from over 10,000 mol. wt. to greater than 100,000 mol. wt. depending on the molecular weight of the tetra-functionally activated polymer starting materials.

Other types of multifunctional polymers can easily be synthesized using routine synthesis. However, care should be taken to produce multi-arm products with consistent arm lengths to avoid stearic hindrance of the reactive groups.

Accordingly, activated polymers that are suitable for use in the present invention may have a variety of geometric shapes and configurations.

Compound Core

As described above, each of the compounds has multiple functional groups, either sulfhydryl groups or sulfhydryl-reactive groups. The non-reactive remainder of the compound is considered to be its "core". At least one of the two compounds must have a polymer core in order to form an efficient gel matrix. When one of the compounds contains a polymer core, the other compound can be a small organic molecule with multiple sulfhydryl-reactive groups. However, for most applications, it is preferred for both compounds to have the same or a different polymer core.

The polymer core may be a synthetic polyamino acid, a polysaccharide, or a synthetic polymer. A preferred polymer core material is a synthetic hydrophilic polymer. Suitable synthetic hydrophilic polymers include, inter alia, polyalkylene oxide, such as polyethylene oxide (($CH_2CH_2O)_n$), polypropylene oxide (($CH(CH_3)CH_2O)_n$) or a polyethylene/polypropylene oxide mixture (($CH_2CH_2O)_n$—($CH(CH_3)CH_2O)_n$). A particularly preferred synthetic hydrophilic polymer is a polyethylene glycol (PEG) having a molecular weight within the range of about 100 to about 100,000 mol. wt., more preferably about 1,000 to about 20,000 mol. wt. More preferably still, when the polymer core is polyethylene glycol, it generally has a molecular weight within the range of about 7,500 to about 20,000 mol. wt. Most preferably, the polyethylene glycol has a molecular weight of approximately 10,000 mol. wt.

Multifunctionally activated polyalkylene oxides, such as polyethylene glycol, are commercially Available, and are also easily prepared using known methods. For example, see Chapter 22 of *Poly(ethylene Glycol) Chemistry: Biotechnical and Biomedical Applications*, J. Milton Harris, ed., Plenum Press, NY (1992); and Shearwater Polymers, Inc. Catalog, *Polyethylene Glycol Derivatives*, Huntsville, Ala. (1997–1998). For use as a tissue sealant, the preferred combination of activated polymers is as follows: the sulfhydry-reactive group-containing compound is the tetrafunctional PEG, pentaerythritol poly(ethylene glycol) ether tetra-succinimidyl glutarate (10,000 mol. wt.); and the sulfhydryl group-containing compound is the tetrafunctional PEG, pentaerythritol poly(ethylene glycol) ether tetra-sulfhydryl (10,000 mol. wt.). In both cases, these "four-arm" PEGs are formed by ethoxylation of pentaerythritol, where each of the four chains is approximately 2,500 mol. wt., and then derivatized to introduce the functional groups onto each of the four arms. Also preferred are analogous poly(ethylene glycol)-like compounds polymerized from di-glycerol instead of pentaerythritol.

Figure 2:
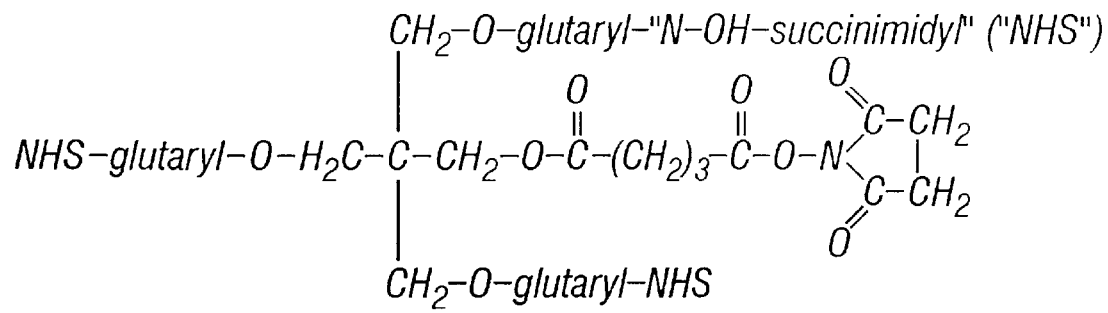
FIG. 2 depicts the structure of a low molecular weight multi-functional reactive compound.

When only one of the reactive compounds comprises a polymer core, the other reactive compound is a multifunctionally active small organic molecule. Such compounds include the di-functional di-succinimidyl esters and di-maleimidyl compounds, as well as other well known commercially available compounds (Pierce Chemical Co., Rockford, Ill.). In addition, one of skill in the art could easily synthesize a low molecular weight multi-functional reactive compound using routine organic chemistry techniques. On such compound is shown in FIG. 2, which is a penta-erythritol coupled to four glutarates, with each arm capped with N-hydroxy-succinimidyl esters (NHS). Analogous compounds can be synthesized from inositol (radiating 6 arm), lactitol (9 arm) or sorbitol (linear 6-arm). The end-capped reactive group can just as easily be sulfhydryl, maleimidyl, vinyl-sulfone, etc., instead of NHS. The polymer or the small molecule can carry either reactive end group as long as there are reactive pairs in the composition such as NHS and SH, maleimidyl and SH, etc.

Reactive Groups and Matrix Linkages

In the present invention, the linkage, Z, comprises a covalent bond between the sulfur atom in the sulfhydryl group-containing compound and, e.g., <* the carbon or sulfur atom in the sulfhydryl-reactive group-containing compound. Accordingly, the linkage may be a thioester, a thioether, a disulfide, or the like. A wide variety of sulfhydryl-reactive groups and the types of linkages they form when reacted with sulfhydryl groups are well known in the scientific literature. For example, see Bodanszky, M., *Principles of Peptide Synthesis*, 2nd ed., pages 21 to 37, Springer-Verlag, Berlin (1993); and Lundbland, R. L., *Chemical Reagents for Protein Modification*, 2nd ed., Chapter 6, CRC Press, Boca Raton, Fla. (1991).

For most applications, sulfhydryl reactive groups that react with sulfhydryl groups to form thioester linkages are preferred. Such compounds are depicted in FIG. 1 and include, inter alia, the following compounds, with the numbers in parentheses corresponding to the structures shown in FIG. 1: mixed anhydrides, such as PEG-glutaryl-acetyl-anhydride (1), PEG-glutaryl-isovaleryl-anhydride (2), PEG-glutaryl-pivalyl-anhydride (3) and related compounds as presented in Bodanszky, p. 23; Ester derivatives of phosphorus, such as structures (4) and (5); ester derivatives of p-nitrophenol (6) of p-nitrothiophenol (7), of pentafluorophenol (8), of structure (9) and related active esters as presented by Bodanszky, pp. 31–32, and Table 2; esters of substituted hydroxylamines, such as those of N-hydroxy-phthalimide (10), N-hydroxy-succinimide (11), and N-hydroxy-glutarimide (12), as well as related structures in Bodanszky; Table 3; esters of 1-hydroxybenzotriazole (13), 3-hydroxy-3,4-dihydro-benzotriazine-4-one (14) and 3-hydroxy-3,4-dihydro-quinazoline-4-one; derivatives of carbonylimidazole; and isocyanates. With these compounds, auxiliary reagents can also be used to facilitate bond formation, such as 1-ethyl-3-[3-dimethylaminopropyl] carbodiimide can be used to facilitate coupling of carboxyl groups (i.e., glutarate and succinate) with sulfhydryl groups.

In addition to the sulfhydryl reactive compounds that form thioester linkages, various other compounds can be utilized that form other types of linkages. For example, compounds that contain methyl imidate derivatives form imido-thioester linkages with sulfhydryl groups. Alternatively, sulfhydryl reactive groups can be employed that form disulfide bonds with sulfhydryl groups, such as ortho pyridyl disulfide, 3-nitro-2-pyridenesulfenyl, 2-nitro-5-thiocyanobenzoic acid, 5,5'-dithio-bis(2-nitrobenzoic acid), derivatives of methane-thiosulfate, and 2,4-dinitrophenyl cysteinyl disulfides. In such instances, auxiliary reagents, such as the hydrogen peroxide or di-tert-butyl ester of azodicarboxylic acid, can be used to facilitiate disulfide bond formation.

Yet another class of sulfhydryl reactive groups form thioether bonds with sulfhydryl groups. Such groups include, inter alia, iodoacetamide, N-ethylmaleimide and other maleimides, including dextran maleimides, mono-bromo-bimane and related compounds, vinylsulfones, epoxides, derivatives of O-methyl-isourea, ethyleneimines, aziridines, and 4-(aminosulfonyl-)7-fluoro-2,1,3-benzoxadiazole.

Chain Extenders

Functional groups may be directly attached to the compound core, or they may be indirectly attached through a chain extender. Such chain extenders are well known in the art. See, for example, PCT WO 97/22371, which describes "linking groups" that would be suitable for use as chain extenders in the compositions of the present invention. Chain extenders are useful to avoid stearic hindrance problems that are sometimes associated with the formation of direct linkages between molecules. Alternatively, chain extenders may be used to link several multifunctionally activated compounds together to make larger molecules. In a particularly preferred embodiment, the chain extender can also be used to alter the degradative properties of the compositions after administration and resultant gel formation. For example, chain extenders can be incorporated into one or both of the multifunctionally activated polymers to promote hydrolysis, to discourage hydrolysis, or to provide a site for enzymatic degradation. Chain extenders can also activate or suppress activity of sulfhydryl and sulfhydryl-reactive groups. For example, electron-withdrawing groups within one or two carbons of the sulfhydryl group would be expected to diminish its effectiveness in coupling, due to a lowering of nucleophilicity. Double-bond carbon and carbonyl carbon would be anticipated to have this effect. Bulky nearby groups for either partner are anticipated to diminish coupling rates, due to steric hindrance. Electron-withdrawing groups adjacent to the reactive carbonyl of glutaryl-N-hydroxysuccinimidyl would be anticipated to make this carbonyl carbon even more reactive with the sulfhydryl partner.

Chain extenders may provide sites for degradation, i.e., hydrolysable sites. Examples of hydrolysable chain extenders include, inter alia, alpha-hydroxy acids such as lactic acid and glycolic acid; poly(lactones) such as caprolactone, valerolactone, gamma butyl lactone and p-dioxanone; poly(amino acids); poly(anhydrides) such as glutarate and succinate; poly(orthoesters); poly(orthocarbonates) such as trimethylene carbonate; and poly(phosphoesters). Examples of non-degradable chain extenders include, inter alia, succinimide, propionic acid and carboxymethylate. See, for example, PCT WO 99/07417. Examples of enzymatically degradable chain extenders include Leu-Gly-Pro-Ala, which is degraded by collagenase; and Gly-Pro-Lys, which is degraded by plasmin.

Gel Strength and Gel Time

The compositions of the present invention are formulated to exhibit adequate strength and rapid gel time. The elastic modulus, G', is the preferred measure of gel strength. Preferred compositions for use as tissue sealants can achieve a gel strength of about $10^3$ to $10^8$ dynes/cm$^2$, and more preferably $10^4$ to $10^7$ dynes/cm$^2$. Preferred compositions for use as hemostatic agents or for adhesion prevention have a gel strength of at least $10^2$ to $10^4$ dynes/cm$^2$ if a soft gel is desired, or $10^5$ to $10^8$ dynes/cm$^2$ if a harder matrix is desired.

The gel time of preferred formulations is less than 60 seconds, more preferably less than 30 seconds, and most preferably less than 15 seconds. The fast gel time ensures maximum material at the site to be treated and sufficient mechanical properties.

Optional Composition Constituents

In addition to the reactive compounds, the compositions of the present invention may also contain other compounds, which may be included in one or both of the components of the two-component compositions, or may be separately administered. In one embodiment, these compounds may become covalently incorporated into the matrix itself by becoming crosslinked to one or both of the reactive compounds after they are mixed together. In another embodiment, such as would be the case if the compound was unreactive with either of the reactive compounds, the compound may be administered in such a way that it become physically or ionically associated with the matrix-forming compounds after mixing, and thus become part of the matrix itself.

Additional compounds that may be added are glycosaminoglycans and proteins. Suitable glycosaminoglycans include, inter alia, hyaluronic acid, chitin, chondroitin sulfate A, B, or C, keratin sulfate, keratosulfate and heparin, and derivatives thereof. In another embodiment, proteins can be added for a variety of purposes. For example, collagen may improve biocompatibility of the matrix, including the potential colonization by cells, promotion of would healing, etc. Collagen and any amino group-containing proteins would also contribute to the structural integrity of the matrix by becoming crosslinked thereto along with the other matrix components. In particular, if PEG-succinimidyl esters are used, the amide bonds formed with collagen will be more stable to hydrolytic degradation than the bonds formed by the reaction of succinimidyl esters and sulfhydryls.

Suitable proteins include, inter alia, collagen, fibronectin, gelatin and albumin, as well as peptide fragments thereof. Particularly preferred is collagen, which may be in the form of afibrillar, microfibrillar or fibrillar collagen. Types I and III collagen isolated from bovine corium or human placenta, or prepared by recombinant DNA methods, are suitable. See PCT WO 90/05755 for a description of suitable collagens and collagen derivatives. It should be understood that when adding collagen to the composition, it is important to adjust the concentration of the other composition components to avoid precipitation.

Additional constituents which may be added to the composition include antibiotics, growth factors, hemostatic proteins (such as thrombin, fibrin, fibrinogen, the blood factors, etc.), cells, genes, DNA, etc.

Composition Formulation

The compositions of the present invention comprise two separate parts, or "components", which may be in liquid or solid form. In a preferred embodiment, both components are liquids, such that each can be easily applied separately to the site of administration. Accordingly, one of the components may be in the form of a dry powder that becomes mixed with the second component, which is in liquid form, when each are sprayed separately onto the tissue, or by mixing at the tissue site. It is also possible to have both components delivered to the site as powders, to be mixed with buffer at the site of administration.

In an alternative embodiment, both components can be mixed together in a single aqueous medium in which they are both unreactive, i.e. such as in a low pH buffer. Thereafter, they can be sprayed onto the tissue site along with a high pH buffer, after which they will rapidly react and form a gel. This embodiment is described in Example 9.

The concentration of the reactive compounds in each of the composition components necessarily depends on a number of factors. For example, if the composition components are each 4-arm PEGs (i.e. PEG-PEG compositions), a concentration of 20–25% by weight in each of the two components before mixing results in a gel after mixing with an elastic modulus, G', of approximately $10^5$–$10^6$ dynes/cm$^2$, which is adequate for use as a surgical sealant. Using methylated collagen and 4-arm succinimidyl PEG, concentrations of 2–4% and 0.2–0.4%, respectively, result in gels with cohesive strengths that are comparable to PEG-PEG gels at 10–15%. Using albumin as one of the components, concentrations of 30% or more achieve a similar cohesive strength. The appropriate concentration of the compound, and other optional ingredients, in each component, and thus the relative concentration of the matrix components in the final gel matrix, can easily be optimized to achieve the desired gelation time and gel strength using routine experimentation. Using the preferred four-arm PEGs described above, the synthetic polymer is generally present at a concentration of 2 to 50% (w/v), and more preferably 10–25%.

The liquid components of the compositions of the present invention are each separately prepared by adding the activated synthetic polymer (in dry form or as a concentrated solution) to a liquid medium. Suitable liquid media include aqueous buffer solutions, such as monobasic sodium phosphate/dibasic sodium phosphate, sodium carbonate/sodium bicarbonate, glutamate or acetate, at a concentration of 0.5 to 300 mM. In general, the sulfhydryl-reactive PEG is prepared in water or a dilute buffer, with a pH of between around 5 to 6. Buffers with pKs between about 8 to 10.5 for preparing the sulfhydryl-PEG component are useful to achieve fast gelation time of compositions containing mixtures of sulfhydryl-PEG/SG-PEG. These include carbonate, borate and AMPSO (3-[(1,1-dimethyl-2-hydroxyethyl) amino]2-hydroxy-propane-sulfonic acid). In contrast, using a combination of maleimidyl PEG and sulfhydryl-PEG, a pH of around 5 to 9 is preferred for the liquid medium used to prepare the sulfhydryl PEG. A particularly preferred composition for hemostatic applications to actively bleeding tissue sites comprises a mixture of maleimidyl and succinimidyl PEG as the first component, and sulfhydryl PEG as the second component. Such compositions produce gels with enhanced biodegradability and superior gel times when compared to compositions having only maleimidyl PEG or succinimicyl PEG alone.

The pH of the aqueous buffer solution that is used for each of the two (or more) composition components should be adjusted using routine optimization to achieve a final pH that is conducive to rapid gelation, without causing instantaneous gelation which interferes with the delivery process. For example, both amino PEG and sulfhydryl PEG need a basic pH to enhance nucleophilicity. The effects of pH on gel time are discussed below in the Examples.

Use and Administration

The compositions of the present invention are generally delivered to the site of administration in such a way that the two (or more) individual components of the composition come into contact with one another for the first time at the site of administration, or immediately preceding administration. Thus, the compositions of the present invention are preferably delivered to the site of administration using an apparatus that allows the two components to be delivered separately. Such delivery systems usually involve two-compartment single exit or dual exit spray devices. Alternatively, the two components can be delivered separately using any type of controllable extrusion system, or they can be delivered manually in the form of separate pastes, liquids or dry powders, and mixed together manually at the site of administration. Many devices that are adapted for delivery of two-component tissue sealants/hemostatic agents are well known in the art and can also be used in the practice of the present invention.

Yet another way of delivering the compositions of the present invention is to prepare the two reactive components (or the single reactive component in the case of sulfhydryl-containing components that are designed to form disulfide bonds) in inactive form as either a liquid or powder. Such compositions can then be activated after application to the tissue site, or immediately beforehand, by applying an activator. In one embodiment, the activator is a buffer solution having a pH that will activate the composition once mixed therewith. See Example 12 for a description of a sulfhydryl-containing PEG composition that is maintained at a low pH until administration, then mixed with a high pH buffer at the application site to initiate gelation.

The compositions of the present invention can be used in a variety of different pharmaceutical applications. In general, the compositions described herein can be adapted for use in any tissue engineering application where synthetic gel matrices are currently being utilized. For example, the compositions of the present invention are useful as tissue sealants, in tissue augmentation, in tissue repair, as hemostatic agents, in preventing tissue adhesions, in providing surface modifications, and in drug/cell/gene delivery applications. One of skill in the art could easily determine the appropriate administration protocol to use with any composition having a known gel strength and gelation time based on the principles described herein and well known scientific principles. A more detailed description of several specific applications is given below:

Tissue Sealants & Adhesives

In a preferred application, the compositions described herein can be used for medical conditions that require a coating or sealing layer to prevent the leakage of gases, liquid or solids. The method entails applying both components to the damaged tissue or organ to seal 1) vascular and or other tissues or organs to stop or minimize the flow of blood; 2) thoracic tissue to stop or minimize the leakage of air; 3) gastrointestinal tract or pancreatic tissue to stop or minimize the leakage of fecal or tissue contents; 4) bladder or ureters to stop or minimize the leakage of urine; 5) dura to stop or minimize the leakage of CSF; and 6) skin or serosal tissue to stop the leakage of serosal fluid.

These compositions may also be used to adhere tissues together such as small vessels, nerves or dermal tissue. The material can be used 1) by applying it to the surface of one tissue and then a second tissue may be rapidly pressed against the first tissue or 2) by bringing the tissues in close juxtaposition and then applying the material.

Surgical Adhesions

A preferred application is a method of reducing the formation of adhesions after a surgical procedure in a patient. The method entails applying the material onto the damaged tissue or organ either by spraying both components together or by applying previously admixed components. The components will react together to form a hydrogel on the tissue surface. The medical procedures include gynecological, abdominal, neurosurgical, cardiac, and orthopedic indications.

Drug Delivery

A preferred application is a method of locally applying a biologically active substance to patients. The active substance can be delivered in conjunction with the two components such that the material can form in situ or as a preformed implant. The active substance can be either released through diffusion controlled processes or may be covalently bound to the components such that it will be released as the resulting hydrogel degrades.

The biologically active substances can be any of a variety of organic and inorganic materials, including proteins, carbohydrates, and nucleic acids. Specific examples include enzymes, antibiotics, antineoplastic agents, cytokines, local anesthetics, hormones, antiangiogenic agents, antibodies, neurotransmitters, psychoactive drugs, drugs affecting reproductive organs, and therapeutic oligonucleotides.

Modification of Implants

A preferred application is a method of applying coatings to implants to affect the surface properties of implants or to help adhere implants to tissue surfaces. A coat of components may be applied to 1) vascular grafts, stents to minimize or stop the leakage of blood or serosal fluid from these devices; 2) catheters or breast implants to reduce or stop excessive fibrosis; 3) artificial patches or meshes to minimize excessive fibrosis and to help adhere the implants to tissue surfaces.

Delivery of Cells or Genes

A preferred application of the compositions is to encapsulate and thereby deliver cells or genes, which includes material from natural sources or synthetic DNA, RNA and their respective antisense forms, to a desired site. The cells can include mesenchymal stem cells, epithelial cells and neuroectodermal cells. The cells may either be allogeneic or xenogenic in origin.

EXAMPLES

Example 1

Preparation of a Two-Component Tissue Sealant Composition a. First Component

Pentaerythritol poly(ethylene glycol)ether tetra-succinimidyl glutarate ("SG-PEG") (mol. wt. 10,000) is dissolved in 0.5 mM sodium phosphate pH 6.0 at a concentration of 20% w/v. (This solution is not stable in aqueous media due to the susceptibility of the active ester to hydrolysis and should be used within one hour of preparation).

b. Second Component

Pentaerythritol poly(ethylene glycol)ether tetra-sulfhydryl (mol. wt. 10,000) is dissolved in 300 mM sodium phosphate/sodium carbonate buffer ("P/C buffer"), pH 9.6, at a concentration of 20% w/v. P/C buffer is prepared as follows: 300 mM sodium monobasic phosphate is mixed with 300 mM sodium carbonate to achieve pH 9.6. The final molarity is approximately 117 mm phosphate and 183 mM carbonate. This solution is stable in aqueous media, but care should be taken to prevent the exposure of the solution to oxygen to prevent oxidation to disulfide. Although pH is preferred for certain compositions, a pH of 8 to 10.5 is generally believed to be suitable for use in the practice of the present invention.

Example 2

Surgical Sealing of Arteries

The right carotid artery of New Zealand white rabbits is exposed. The rabbits are treated with 200 U/kg of heparin and the vessel is clamped proximally and distally using atraumatic vascular clamps. A puncture hole is made in the carotid artery using a 27G needle. The control rabbits are treated with tamponade until hemostasis is achieved. For the treated rabbits, approximately 0.5 mL of each of the two components of the compositions prepared as described in Example 1 are delivered to the defect site using a two component sprayer (Duo Flow, Hemaedics, Malibu, Calif.). After the material is allowed to set for 30 sec, the clamps are removed and the time to hemostasis and the blood loss are measured. The arteries of the control rabbits also remain clamped for 30 sec for consistency. The results are shown in Table 1.

TABLE 1

Blood Loss and Time to Hemostasis as a Function of Treatment

| Treatment | Blood Loss (g) | Time to Hemostasis (sec) |
| --- | --- | --- |
| Tamponade (n = 18) | 5.7 ± 3.4 | 144 ± 34 |
| Hydrogel (n = 17) | 1.0 ± 2.5 | 31 ± 65 |

The above results illustrate that the composition significantly reduces the amount of blood loss and time to hemostasis from a punctured artery.

Example 3

Surgical Sealing of a ePTFE Graft

The dogs are treated with heparin to achieve an activated clotting time of greater than 480 sec. The left iliac of the dogs is exposed and isolated using atraumatic vascular clamps placed distally and proximally. A 5 cm segment of the artery is excised and replaced with an ePTFE (polythetrafluoroethylene) graft of the same diameter. Prior to the completion of the anastamosis, the graft was de-aired using a 27G needle. Approximately 3.0 mL of each of the two components of the composition prepared according to Example 1 is delivered to the defect site using a two component sprayer (Cohesion Technologies, Inc., Palo Alto, Calif.). After the material is allowed to set for 30 sec, the clamps are removed and the time to hemostasis and the blood loss are measured. The procedure was repeated on the left iliac, with the exception of material application. The right iliac received only tamponade treatment. The results are shown in Table 2.

TABLE 2

Blood Loss and Time to Hemostasis as a Function of Treatment

| Treatment | Blood Loss (g) | Time to Hemostasis (sec) |
| --- | --- | --- |
| Tamponade (n = 2) | 244, 180 | >15, >15 |
| Hydrogel (n = 2) | 18, 7 | 3.3, 2.3 |

The above results illustrate that this composition significantly reduces the amount of blood loss and time to hemostasis from an ePTFE anastamosis.

Example 4

Enhanced Biocompatibility of Thioester-linked Formulations

Up to six subcutaneous pockets are made on the backs of New Zealand white rabbits. Approximately 1.0 mL of each of the components of the composition described in Example 1 is delivered to the defect site using a two component sprayer (Cohesion Technologies, Inc., Palo Alto, Calif.) for liquid formulations or a spatula for formulations that are gelled ex-vivo. The grading key is shown in Table 3 and the results are shown in Table 4.

TABLE 3

Grading Key for Biocompatibility Experiments

| Score | Gross Observations | Histological Observations |
|---|---|---|
| − | all tissues appeared normal | all tissues appeared normal, no inflammation |
| + | mild foreign body response | mild inflammation |
| ++ | moderate foreign body response | moderate inflammation |
| +++ | marked foreign body response | marked inflammation |
| ++++ | severe foreign body response | severe inflammation |

TABLE 4

Results for Biocompatibility Experiments

| Test | Description | Gross Observations | Histological Observations |
|---|---|---|---|
| A | surgical control | − | + |
| B | fibrillar collagen | − | + |
| C | 20% w/v tetra-SG PEG 10,000 + 20% w/v tetra-amino PEG 10,000 | ++++ | ++++ |
| D | 20% w/v tetra-SG PEG 10,000 + 20% w/v tetra-sulfhydryl PEG 10,000 | ++ | ++ |
| E | 20% w/v tetra-SG PEG 10,000 + 20% w/v tetra-amino PEG 10,000; gelled ex-vivo; treated with mono-SG PEG 5000 | + | ++ |
| F | 20% w/v tetra-SG PEG 10,000 + 20% w/v di-sulfhydryl PEG 3,400; gelled ex-vivo; treated with di-amino PEG 3400 | ++++ | ++++ |

Experiments A and B show a mild gross and histological response of fibrillar collagen (Collagen Corporation, Palo Alto, Calif.) and the surgical control. Experiment C shows a severe response to hydrogels made with amino-PEG. The response consists of thick encapsulation of the hydrogel and abscess formation. By substitution of sulfhydryl-PEG for amino-PEG, as in Experiment D, the biocompatibility of the hydrogel is significantly improved. Experiment E involves forming an amino hydrogel ex-vivo and incubating the hydrogel in a solution of mono-SG PEG, 5000 mol. wt. During the incubation period, the mono-SG PEG reacts with the free amines present on the hydrogel network, thus reducing the amount of free amines on the polymeric network. This treatment enhances the biocompatibility of the hydrogel. Experiment F involves forming a sulfhydryl hydrogel ex-vivo and incubating the hydrogel in a solution of mono-SG PEG, 5000 mol. wt. During the incubation period, the di-amino PEG reacts with the free SG groups present on the hydrogel network, thus increasing the amount of free amines on the polymeric network. This treatment decreases the biocompatibility of the hydrogel. Thus, these results show the enhanced biocompatibility of sulfhydryl formulations over amino formulations.

Example 5

Effect of Buffer and Reactive Group on Gel Times

A desirable characteristic of the compositions described herein is their ability to rapidly achieve gelation. In this experiment, the effects of buffer strength and composition on gelation kinetics are studied. For all experiments, the tetra-functional SG PEG described in Example 1 is dissolved in 0.5 mM sodium phosphate, pH 6.0, and the tetra-sulfhydryl PEG described in Example 1, or the equivalent tetra-amino PEG is dissolved in the buffer listed in Table 5.

TABLE 5

Effect of Phosphate vs. Carbonate Buffer on Amino and Sulfhydryl Formulations

| Test | Formulation | Buffer | Gel Time (sec) |
|---|---|---|---|
| A | 10% w/v tetra-SG PEG 10,000 + 10% w/v tetra-amino PEG 10,000 | 300 mM dibasic sodium phosphate pH 9 | 16 |
| B | 10% w/v tetra-SG PEG 10,000 + 10% w/v tetra-sulfhydryl PEG 10,000 | 300 mM dibasic sodium phosphate pH 9 | 55 |
| C | 10% w/v tetra-SG PEG 10,000 + 10% w/v tetra-amino PEG 10,000 | 300 mM sodium carbonate pH 9 | 14 |
| D | 10% w/v tetra-SG PEG 10,000 + 10% w/v tetra-sulfhydryl PEG 10,000 | 300 mM sodium carbonate pH 9 | 9 |
| E | 10% w/v tetra-SG PEG 10,000 + 10% w/v tetra-sulfhydryl PEG 10,000 | P/C Buffer pH 9.6 | 3 |

Experiments A and B show the difference in gel times in amino formulations and sulfhydryl formulations in phosphate buffer. In this buffer, an increase in gelation rate is observed for sulfhydryl formulations compared to amino formulations. Experiments C and D show the difference in gelation times in amino formulations and sulfhydryl formulations in carbonate buffer. As shown, a decrease in gel time is observed for sulfhydryl formulations in carbonate buffer. In the preferred P/C Buffer, a gel time of 3 seconds is observed.

Example 6

Rheometric Measurements

The first component (tetra-functional Sulfhydryl-PEG, 10,000 mol. wt.) was prepared according to Example 1 and suspended in P/C Buffer. The second component (tetra-functional SG-PEG, 10,000 mol. wt.) was prepared according to Example 1 in 0.5 mM phosphate, pH 6.0. The two components (0.6 ml each) were loaded in a dual-syringe device with joiner and cannula. The cannula contained a mixing element. The solutions were mixed, and the resultant mixture was immediately delivered into a parallel plate cell of a Rheometrics Fluids Spectrometer 8500 (Rheometrics, Inc., Piscataway, N.J.). The upper platen had a diameter of 25 mm, and the gap between upper and lower parallel plates was 1.5 mm.

Figure 3:
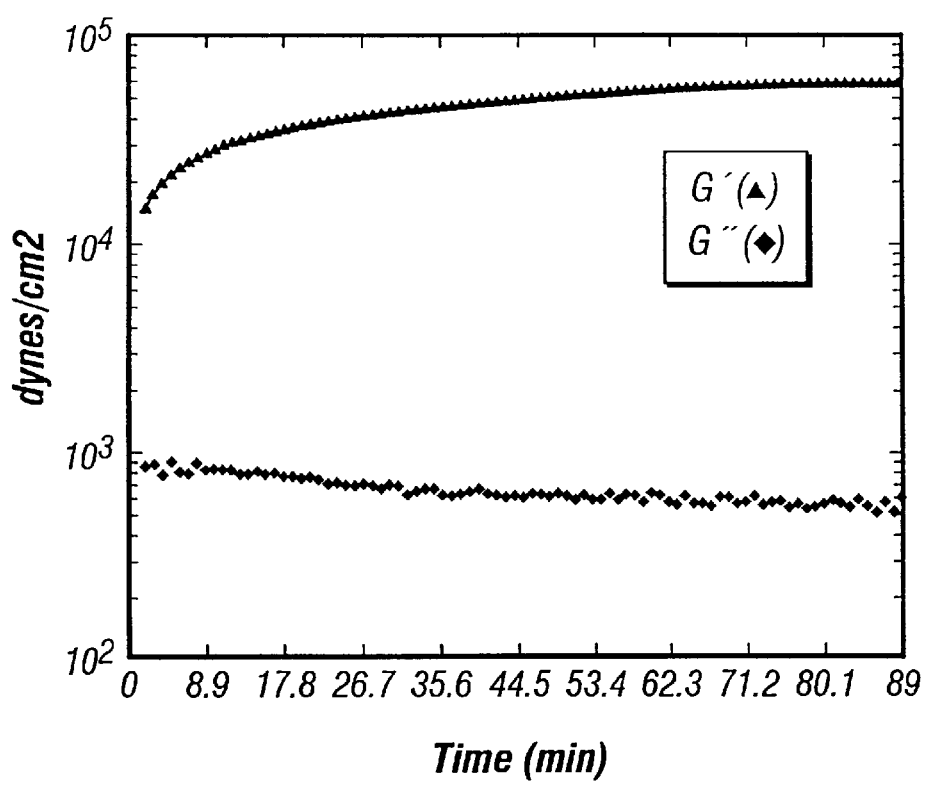
FIG. 3 depicts the rheometric measurements of gelation of a mixture of reactive tetrafunctional polyethylene glycols.

Gelation began immediately upon mixing of the formulation. The instrument was started, and G' and G" (elastic and viscous moduli, respectively) were measured at 1% strain and 1 radian/sec. In less than a minute, G' was near $10^4$ dynes/cm$^2$, which is characteristic of a soft rubbery material. G' began to plateau within 15 min, and continued to rise very gradually for more than an hour afterwards. G" was in the order of $10^2$ dynes/cm$^2$, and declined gradually. These results are consistent with a rapidly gelling material. G' and G" for the unreacted starting materials was about 1–10 dynes/cm$^2$. These results are depicted in FIG. 3.

In this experiment, the rheometer cannot precisely quantitate G' and G" below about 50 dynes/cm$^2$. In addition, the gelation occurred so rapidly that the mixture only filled 30 to 95% of the desired space—there was gelled fluid surrounding the plate, but not between the plates. Even with these limitations, a measurement of the elastic (G') and viscous modulus (G") as a function of time can still be made, and the kinetics of gelation can be followed. As indicated in this experiment, a G' of greater than $10^2$ dynes/cm$^2$ in less than one minute indicates rapid gelation.

Example 7

Effects of Buffers on Gel Time Using Sulfhydryl-PEG and N-hydroxy-succinimidyl-PEG (NHS-PEG)

All tests were done with 50 ml of 20% (w/v) 4 arm, 10,000 mol. wt., tetrafunctional SG-PEG mixed with 50 ml of 20% (w/v) 4 arm, 10,000 mol. wt., tetra-functional sulfhydryl-PEG). Different buffers were used, and the times to gel were noted. The SG-PEG was dissolved in 0.5 mM phosphate, pH 6.0 for all tests. The sulfhydryl-PEG was dissolved in the buffers given below at a pH of 9.6 and times to gel are noted.

TABLE 6

Effect Buffers on Gelation Time.

| Test | Buffer | Gel Time (Sec) |
| --- | --- | --- |
| A | P/C Buffer | 8 |
| B | 150 mM phosphate | 35 |
| C | 58 mM phosphate 91 mM sodium chloride | 138 |
| D | 58 mM phosphate 91 mM borate | <19 |
| E | 58 mM phosphate 91 mM AMPSO* | 8 |

*(3[1,1-dimethyl-2-hydroxy-ethyl)amino]-2-hydroxypropane-sulfonic acid

As shown, buffers with pKs between 8 and 10.5 (borate, 8.1; carbonate, 10.3; AMPSO, 9.0), and mixtures thereof, are suitable

Example 8

Sulfhydryl-Reactive PEGs

The gelation characteristics of several different formulations are described below:

8a: Gelation of Di Functional Maleimidyl-PEG, 3400 mol. wt. (MAL-PEG) with Tetra-Sulfhydryl PEG, 10,000 mol. wt.

A 20% (w/v) solution of MAL-PEG in 0.5 mM sodium phosphate, pH 6.0, was mixed rapidly with an equal volume of 20% (w/v) tetra-sulfhydryl PEG in 150 mM sodium phosphate, pH 5.0. Gelation occurred in 15 sec. The gel became a firm, rubbery solid in a minute or less.

8b: Gelation of Difunctional Iodoacetamide PEG, 3,400 mol. wt. ("IAM-PEG") with Tetra-Sulfhydryl PEG, 10,000 mol. wt.

IAM-PEG was dissolved at 20% (w/v) in 0.5 mM sodium phosphate, pH 6.0, and mixed rapidly with a 20% (w/v) solution of tetra-sulfhydryl PEG in P/C Buffer sodium phosphate-carbonate, pH 9.6. Gelation occurred in less than 40 sec. A firm gel formed within 2 min.

8c: Gelation of Tetra-Sulfhydryl PEG, 10.000 mol. wt., with Dilute Hydrogen Peroxide A 20% (w/v) solution of tetra-sulfhydryl PEG in P/C Buffer, was mixed with an equal volume of 0.1% (w/v) hydrogen peroxide. Gelation occurred in 15 sec. A firm gel formed in less than 2 min.

Example 9

Blood Coagulation Activity of Thrombin Incorporated into PEG Compositions

This experiment demonstrates that hemostatic PEG gels containing active thrombin protein can be formed on tissue.

9a: Thrombin Incorporated into Tetra-Sulfhydryl PEG Gelled with Hydrogen Peroxide 20 mg of tetra-sulfhydryl PEG, 10,000 mol. wt., were dissolved in 80 μl of PC Buffer, and 11 μl of bovine thrombin at 8850 NH units/ml in 0.72 M sodium chloride (Thrombin topical, USP, Gentrac, Inc., Middleton, Wis.) were added. This solution of tetra-sulfhydryl PEG and thrombin was then mixed with 100 μl of 0.1% (w/v) hydrogen peroxide in water, by stirring rapidly in a 1.5 ml plastic tube. The mixture gelled in less than 40 sec, due to oxidation of the sulfhydryl groups to disulfide bonds. After 1.5 min, the gel was a firm, rubbery solid. On top of this gel was layered 200 μl of rabbit blood plasma. The plasma had been separated from citrated blood and contained approximately 11 mM citrate. Just prior to addition, this citrated blood plasma was re-calcified by addition of 8 μl of 0.5 M calcium chloride, to achieve a concentration of about 20 mM calcium. This re-calcified blood plasma was observed to form a fibrin clot 1.5 minutes after layering onto the PEG gel. The clotting reaction was taken as evidence for the presence of active thrombin in the PEG gel.

When control studies are performed, a second oxidized sulfhydryl-PEG gel without thrombin does not clot rabbit plasma until 20 minutes have elapsed. As a further control, re-calcified rabbit plasma is held in an identical plastic tube; and it clots spontaneously after 13 minutes. Therefore, the sulfhydryl-PEG gel without thrombin clots blood no faster than control re-calcified plasma.

When the analogous experiment was attempted with tetra-sulfhydryl PEG and tetra-SG-PEG, plus thrombin, no enhanced clotting time of plasma was observed. Clotting of plasma was delayed beyond 25 minutes. This result is interpreted to indicate that SG-PEG inactivated thrombin, presumably by binding PEG to lysine side chains of thrombin and interfering with its enzymatic activity.

9b: Thrombin Incorporated into LAM-PEG/Sulfhydryl-PEG gel 20 mg of tetra-sulfhydryl PEG, 10,000 mol. wt. are dissolved in 80 μl of PC Buffer along with 11 μl of thrombin, as in 9a. above. 20 mg of LAM-PEG are dissolved in 80 μl of 0.5 mM sodium phosphate, pH 6.0. The two solutions are rapidly mixed in a 1.5 ml plastic tube. The mixture has a gel time less than 30 sec and is a rubbery gel by 1.5 minutes. Re-calcified rabbit plasma (200 μl) is layered on top of the gel, and a fibrin clot forms in this plasma in less than two minutes after layering onto the gel. A control reaction without thrombin forms a fibrin clot more than 18 minutes after layering onto the PEG gel. The rapid formation of a fibrin clot in the sample containing thrombin is taken as evidence for the presence of active thrombin in the PEG gel.

9c: Thrombin Incorporated into NEM-PEG/Sulfhydryl PEG gel 20 mg of tetra-sulfhydryl PEG, 10,000 mol wt., is dissolved in 80 μl of 150 mM sodium phosphate, pH 5.0, along with 11 μl of thrombin, as in 9a above. 20 mg of NEM-PEG are dissolved in 0.5 mM sodium phosphate, pH 6.0. The two solutions are rapidly mixed in a plastic tube. Gelation occurs in 15 sec. 15 gl of P/C Buffer, are layered onto the top of the PEG gel to adjust the pH to 7–9. Then, 200 μl of re-calcified rabbit plasma are added. A fibrin clot formed in 1.5 min. after addition of the plasma. Control gels with no thrombin form a fibrin clot after 30 min. Again, the rapid formation of a fibrin clot in the PEG gel with thrombin is taken as evidence for the presence of active thrombin.

9d: Gelation of Layered Gels with Thrombin

In order to provide a gel formulation from SG-PEG and sulfhydryl-PEG to which thrombin can be added and remain active, a "gel layering" technique can be used. First, the tetra-sulfhydryl-PEG and tetra-Se-PEG gel at 20% solids, prepared according to Example 1 are sprayed onto sheets as described in Example 2. The sheets are coarse fibered collagen hydrated by saline, which simulates a tissue surface. The total volume is approximately 0.5 ml. This formula gels in 18–15 sec. At 16 seconds, a second gel mixture of tetra-sulfhydryl PEG, di-maleimidyl PEG, both at 20% solids, and thrombin (700 NIH units/ml) of total gel mixture, total volume approx. 0.5 ml, are sprayed on top of the first gel. This second gel layer gels at about 2 minutes. At 3 min after the first gel is sprayed, 0.4 ml of re-calcified rabbit blood plasma, prepared as described above are layered on top of the PEG gel. This plasma clots 1.5 minutes after it is layered onto the PEG gel. The formation of a fibrin clot at this early time, compared to a non-thrombin control, is taken as evidence for active thrombin in the PEG gel.

Example 10

Gelation Using Powdered Formulations 10 mg of powdered tetra-SG PEG, 10,000 mol. wt., is spread on the surface of a piece of weighing paper. 10 mg of tetra-sulfhydryl PEG, 10,000 mol. wt., is dissolved in 80 $\mu$l of P/C buffer. The sulfhydryl-PEG solution is loaded into a 1 cc syringe with a Haemedics (Malibu, Calif.) spray head and sprayed onto the SG-PEG on the weighing paper. The sprayed fluid is not stirred or mixed. It begains to gel in 27 seconds and forms a firm, rubbery layer by 2 min. This test shows that components in powdered form are also suitable for use in the present invention.

Example 11

Collagen-Containing Compositions

Methylated collagen is prepared by the following process: bovine corium collagen is solubilized using pepsin and purified as described in U.S. Pat. No. 4,233,360. This purfied, solubilized collagen is precipitated by neutralization into 0.2M sodium phosphate, pH 7.2. The precipitate is isolated by centrifugation to a final concentration of 70 mg/ml. The material is dried for two days, and then pulverized. Dry methanol containing HCl (to 0.1 N) is added (40 ml) and stirred for four days. Collagen is separated from the acidic methanol, vacuum dried and sterilized by irradiation. The final product is disolved in water at a pH of 3–4.

For delivery as a sealant, 10 mg of the methylated collagen, 100 mg of tetra-functional sulfhydryl-PEG, 10,000 mol. wt., and 100 mg of tetra-functional SG PEG, 10,000 mol. wt., are dissolved in water at pH 3–4 to a final volume of 1 ml (first component). The second component is 1 ml of P/C Buffer. Each component is placed in a syringe and mixed and sprayed on the desired test site using a dual-syringe delivery system as described in Example 1. The applied mixture gels in less than 3 seconds.

The adhesive and cohesive properties of the gel are examined in a burst test. This test is conducted on a pressure gauge apparatus (PSI-Tronix, Model PG5000, Tulare, Calif.) connected by a pressure line to a circular sample plate with a 2 mm diameter central orifice. Sealant formulations are sprayed onto the plate to seal the orifice. To simulate bonding of the formulations to tissue, the sample plate has a circular sheet of coarse-fibered collagen fastened to it, with a 2 mm hole pierced into it and displaced 2–3 mm from the sample plate orifice. Burst strength is measured as a function of the pressure it takes to force saline at a flow rate of 5 ml/min through the sealant gel.

The results are given below in Table 7.

TABLE 7

Burst Strength Measurements of Collagen-Containing Compositions

| Material | Burst Strength, mm Hg |
|---|---|
| Sulfhydryl-PEG/SG-PEG | 100–180 |
| Sulfhydryl-PEG/SG-PEG/ Methylated Collagen | 122–205 |

Both formulations have gel times less than 3 seconds. As shown above, the addition of collagen to the formulation enhances burst strength.

Example 12

Synthesis of "12-arm" PEG Compounds

Figure 4A:
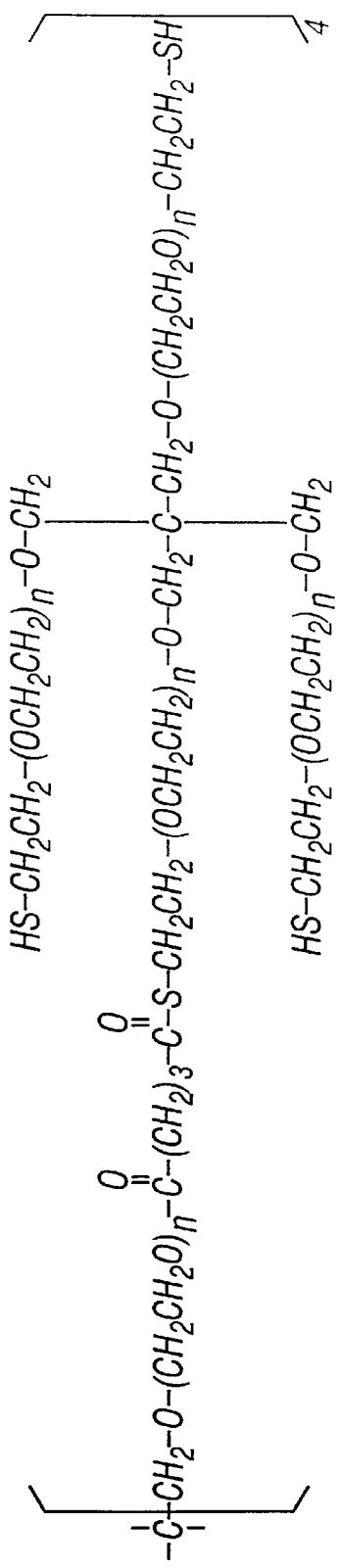
FIG. 4a depicts a "12-arm" sulfhydryl reactive PEG compound as described in Example 13.
Figure 4B:
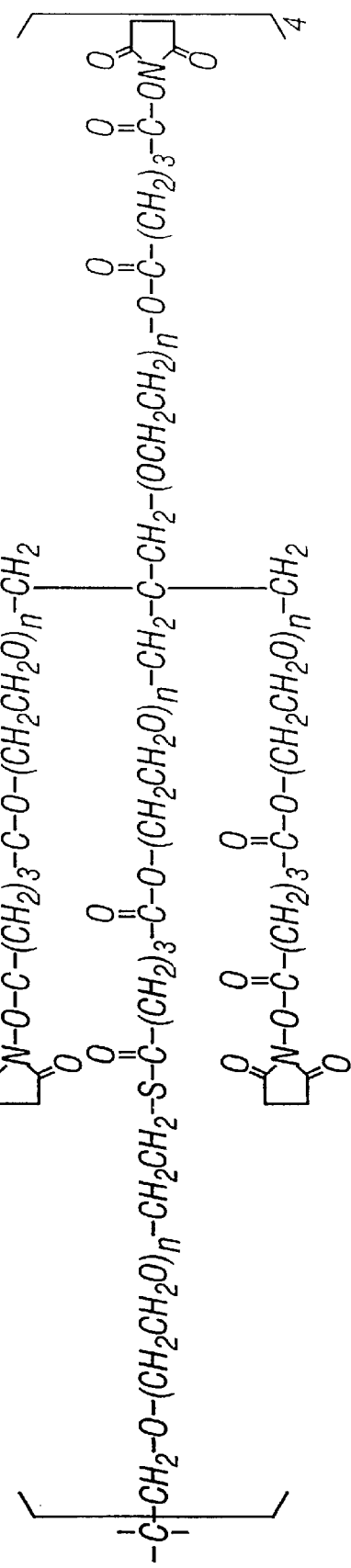
FIG. 4b depicts a "12-arm" succinimidyl reactive PEG compound as described in Example 13.
Figure 5A:
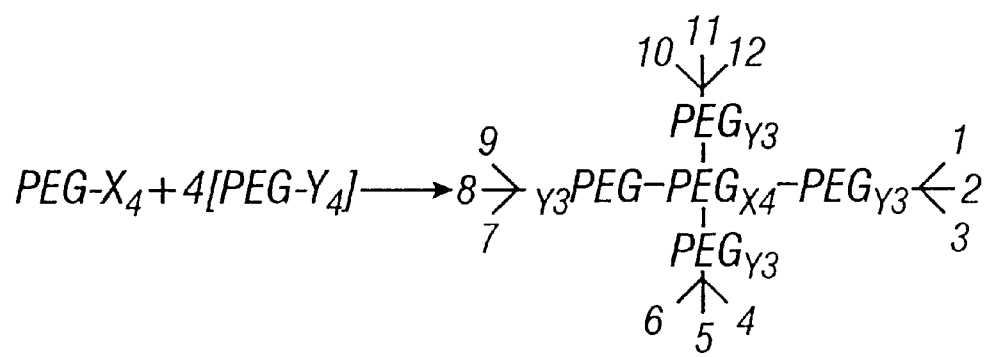
FIG. 5 depicts the formation of two "12-arm" peg compounds from "4-arm" intermediates as described in Example 13.
Figure 5B:
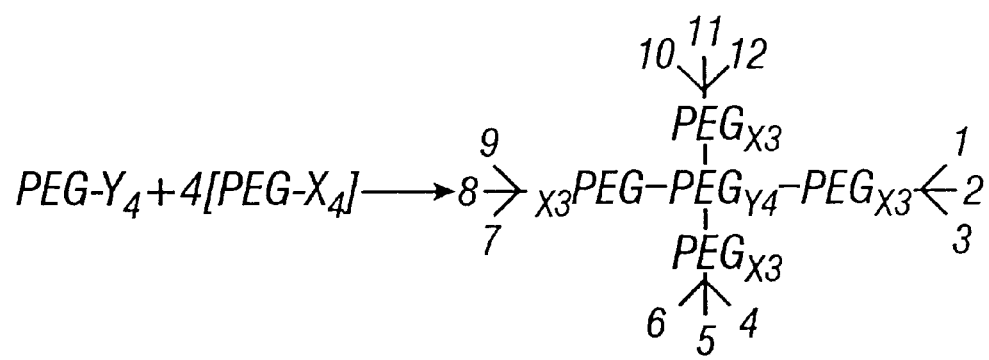

A 12-arm electrophilic PEG compound is formed from 1 mole of 4-arm sulfhydryl PEG, 10,000 mol. wt., and 4 moles of 4-arm SG-PEG, 10,000 mol. wt. The resulting compound is depicted in FIG. 4a. As shown, the compound core is pentaerythritol PEG ether tetra-sulfhydryl and the end functional group is succinimide. As long as the functional groups are reactive with one another to form chemical bonds, the sulfhydryl group, X, can be replaced with other nucleophilic groups, such as $NH_2$, etc., and the succinimidyl group, Y, can be replaced with other electrophilic groups, such as maleimide, carbonyl imidazole, or isocyanate. This method is also used to prepare the 12-arm nucleophilic PEG compound depicted in FIG. 4b by reacting 4 moles of 4-arm sulfhydryl PEG with 1 mole of 4-arm SG-PEG. The formation of these compounds from their respective 4-arm intermediates are also shown in FIG. 5. It should be understood that such reactions produce a heterogeneous population of activated PEG product, some having less than 12 arms, and some having more than 12 arms. As used herein, a "12-arm" PEG also refers to such heterogeneous reaction products that have an average of about 12 arms on each molecule.

12a: 12 arm Sulfhydryl PEG

Eight grams of pentaerythritol (polyethylene glycol)ether tetra sulfhydryl was dissolved in a mixture of 100 mL of methylene chloride and 100 mL of triethylamine. Two grams of pentaerythritol (polyethylene glycol)ether tetra succinimidyl glutarate in 40 mL of methylene chloride was slowly added with stirring at room temperature under argon overnight. The solvent was removed and the product was isolated by recrystallilzation in ethanol and dried.

12b: 12 arm Succinimidyl PEG

Two grams of pentaerythritol (polyethylene glycol)ether tetra succinimidyl glutarate was dissolved in 50 mL of methylene chloride. 0.5 grams of pentaerythritol (polyethylene glycol)ether tetra amine in 10 mL of methylene chloride was slowly added with stirring at room temperature under argon overnight. The solvent was removed and the product was isolated by recrystallization in ethanol and dried.

When the two compounds were tested for burst strength as described in Example 12, they demonstrated a burst strength of greater than 150 mm Hg and a gel time of less than 2 seconds.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention as set forth in the claims which follow. All publications, patents, and patent applications cited in this specification are incorporated herein by reference as if each such publication, patent, or patent application was specifically and individually indicated to be incorporated herein by reference.

We claim:

1. A biocompatible gel-forming composition for in vivo administration, comprising:
   a first component comprising at least one sulfhydryl group-containing compound in a liquid medium having an alkaline pH, wherein said sulfhydryl group-containing compound is given by the formula Compound$_1$-(SH)$_m$, wherein m≧2; and
   a second component comprising at least one sulfhydryl reactive group-containing compound in either a liquid medium having a neutral or acidic pH or in powder form, wherein said sulfhydryl reactive group-containing compound is given by the formula Compound$_2$-Y$_n$, wherein Y is a sulfhydryl reactive group and wherein n≧2;
   wherein at least one of the first or second components is a polyalkylene oxide and wherein the sulfhydryl groups and the sulfhydryl reactive groups react with one another to form covalent bonds therebetween when said components are mixed together to form a gel in less than one minute.

2. The composition of claim 1, wherein m and n are each 4.

3. The composition of claim 1, wherein m and n are each 12.

4. The composition of claim 1, wherein the first component is a polyalkylene oxide.

5. The composition of claim 1, wherein the second component is a polyalkylene oxide.

6. The composition of claim 1, wherein the first and second components are polyalkylene oxides.

7. The composition of claim 6, wherein the polyalkylene oxides are polyethylene glycol.

8. The composition of claim 1, wherein only one of the first or second components is a polyalkylene oxide.

9. The composition of claim 8, wherein one of the components is a polyalkylene oxide and the other component is a functionally activated succinimidyl or maleimidyl compound which is not a polymer.

10. The composition of claim 1, wherein the covalent bonds are thioester linkages.

11. The composition of claim 1, wherein the covalent bonds are thioether linkages.

12. The composition of claim 1, wherein the covalent bonds are sulfhydryl linkages.

13. The composition of claim 1, further comprising a hemostatic agent.

14. The composition of claim 1, wherein the hemostatic agent is thrombin.

15. The composition of claim 1, wherein the first component is suspended in a buffer solution comprising a mixture of phosphate buffer and carbonate buffer.

16. The composition of claim 2, wherein the second component comprises a mixture of succinimidyl polyalkylene oxide and maleimidyl polyalkylene oxide.

17. A method for treating tissues, comprising the steps of:
   administering to a tissue site a first component comprising at least one sulfhydryl group-containing compound in liquid medium having an alkaline pH, wherein said sulfhydryl group-containing compound is given by the formula Compound$_1$-(SH)$_m$, wherein m≧2; and
   simultaneously or subsequently administering to the tissue site a second component comprising at least one sulfhydryl reactive group-containing compound either a liquid medium having a neutral or acidic pH or in powder form, wherein said sulfhydryl reactive group-containing compound is given by the formula Compound$_2$-Y$_n$, wherein Y is a sulfhydryl reactive group and wherein n≧2, and wherein at least one of the first or second components is a polyalkylene oxide; and
   allowing the sulfhydryl groups and the sulfhydryl reactive groups to react with one another to form covalent bonds therebetween to form a gel in less than one minute.

18. A biocompatible gel-forming composition for in vivo administration with a gel time of less than one minute, comprising:
   polyalkylene oxide-(SH)$_4$ in a liquid medium having a pH of between 8 and 10.5; and
   polyalkylene oxide-Y$_4$, wherein Y is succinimidyl, in a liquid medium having an acidic pH.

19. A biocompatible gel-forming composition for in vivo administration with a gel time of less than one minute, comprising:
   polyalkylene oxide-(SH)$_{12}$ in a liquid medium having an alkaline pH; and
   polyalkylene oxide-Y$_{12}$ in a liquid medium having an acidic pH, wherein Y is a succinimidyl or maleimidyl group.

20. A biocompatible gel-forming composition for in vivo administration, comprising:
   a sulfhydryl group-containing polyalkylene oxide in a liquid medium having an acidic pH, wherein said sulfhydryl group-containing polyalkylene oxide is given by the formula Core-(SH)$_m$, wherein m≧2; and
   a buffer solution with an alkaline pH;
   wherein the sulfhydryl groups react with one another to form covalent bonds therebetween when said components are mixed together to form a gel in less than one minute.

21. A biocompatible gel-forming composition for in vivo administration, comprising:
   at least one sulfhydryl group-containing compound in a liquid medium having an alkaline pH, wherein said sulfhydryl group-containing compound is given by the formula Compound$_1$-(SH)$_m$, wherein m≧2;
   at least one sulfhydryl reactive group-containing compound either a liquid medium having a neutral or acidic pH or in powder form, wherein said sulfhydryl reactive group-containing compound is given by the formula Compound$_2$-Y$_n$, wherein Y is a sulfhydryl reactive group and wherein n≧2; and
   collagen;
   wherein at least one of either the sulfhydryl group-containing compound or the sulfhydryl reactive group-containing compound is a polyalkylene oxide, and wherein the sulfhydryl groups and the sulfhydryl reactive groups are capable of reacting with one another to form covalent bonds therebetween.

22. The composition of claim 21, wherein m and n are each 4.

23. The composition of claim 21, wherein m and n are each 12.

24. The composition of claim 21 wherein the sulfhydryl group-containing compound is a polyalkylene oxide.

25. The composition of claim 21, wherein the sulfhydryl reactive group-containing compound is a polyalkylene oxide.

26. The composition of claim 21, wherein both the sulfhydryl group-containing compound and the sulfhydryl reactive group containing compound are polyalkylene oxides.

27. The composition of claim 26, wherein both the sulfhydryl group-containing compound and the sulfhydryl reactive group-containing compound are polyalkylene oxides.

28. The composition of claim 21, wherein only one of the first or second components is a polyalkylene oxide.

29. The composition of claim 28, wherein one of the components is a polyalkylene oxide and the other component is a functionally activated succinimidyl or maleimidyl compound which is not a polymer.

30. The composition of claim 21, wherein the covalent bonds are thioester linkages.

31. The composition of claim 21, wherein the covalent bonds are thioether linkages.

32. The composition of claim 21, wherein the covalent bonds are sulfhydryl linkages.

33. The composition of claim 21, further comprising a hemostatic agent.

34. The composition of claim 21, wherein the hemostatic agent is thrombin.

35. The composition of claim 21, wherein the sulfhydryl group-containing compound is suspended in a buffer solution comprising a mixture of phosphate buffer and carbonate buffer.

36. The composition of claim 21, wherein the sulfhydryl reactive group-containing compound comprises a mixture of succinimidyl polyalkylene oxide and maleimidyl polyalkylene oxide.

37. The composition of claim 21, wherein the collagen is methylated collagen.

38. A biocompatible gel-forming composition for in vivo administration, comprising:
   (a) a first component in a liquid medium having an acidic pH comprising:
      (i) at least one sulfhydryl group-containing compound given by the formula $Compound_1\text{-}(SH)_m$, wherein $m \geq 2$;
      (ii) at least one sulfhydryl reactive group-containing compound given by the formula $Compound_2\text{-}Y_n$, wherein Y is a sulfhydryl reactive group and wherein $n \geq 2$; and
      (iii) collagen; and
   (b) a second component comprising a buffer having a pH of between 8 and 10.5;
   wherein at least one of either the sulfhydryl group containing compound or the sulfhydryl reactive group containing compound is a polyalkylene oxide.

39. The composition of claim 38, wherein the collagen is methylated collagen.

40. The composition of claim 38, wherein the second component is a buffer solution comprising a mixture of phosphate buffer and carbonate buffer.

* * * * *